United States Patent [19]

Berndtsson

[11] 4,318,399

[45] Mar. 9, 1982

[54] RESPIRATOR APPARATUS

[75] Inventor: Christer Berndtsson, Lidingö, Sweden

[73] Assignee: AGA Aktiebolag, Lidingö, Sweden

[21] Appl. No.: 98,149

[22] Filed: Nov. 28, 1979

[30] Foreign Application Priority Data

Nov. 29, 1978 [SE] Sweden .................... 7812269

[51] Int. Cl.³ .................................. A61M 16/00
[52] U.S. Cl. .......................... 128/204.23; 128/202.22; 128/205.24
[58] Field of Search ............... 128/202.22, 204.21, 128/204.23, 204.26, 205.13, 205.16, 205.24, 204.18, 204.24

[56] References Cited

U.S. PATENT DOCUMENTS

| | | | |
|---|---|---|---|
| 3,333,584 | 8/1967 | Andreasen et al. | 128/204.21 X |
| 3,566,387 | 2/1971 | Schoener et al. | 128/204.23 X |
| 3,877,467 | 4/1975 | Plicchi | 128/202.22 |
| 3,903,881 | 9/1975 | Weigl | 128/204.26 X |
| 4,096,858 | 6/1978 | Eyrick et al. | 128/204.21 X |
| 4,141,354 | 2/1979 | Ismach | 128/204.26 X |
| 4,206,754 | 6/1980 | Cox et al. | 128/204.26 X |

Primary Examiner—Henry J. Recla
Attorney, Agent, or Firm—Pollock, Vande Sande & Priddy

[57] ABSTRACT

Respirators work cyclically with an inspiration phase, in which breathing gas is forced into the lungs of a patient, followed by an expiration phase, in which the supply of breathing gas to the patient is stopped and the patient is exhaling by himself. There is a risk that the patient will have difficulty exhaling. In this case the lung pressure of the patient will be too high unless the gas supply is interrupted at the start of the next following inspiration phase. In order to detect too high lung pressure and to provide such interruption, a pressure sensor is arranged to sense the gas pressure in a gas line connected to the breathing catheter introduced into the lung of the patient. This pressure sensor will normally detect a higher pressure during the inspiration phase than during the expiration phase. Therefore, an operating circuit is arranged to sense the state of the pressure sensor in a predetermined phase position only during the expiration phase. When this circuit detects an overpressure in the predetermined position, it feeds an inhibiting signal to the respirator to prevent the commencement of a subsequent inspiration phase.

12 Claims, 2 Drawing Figures

RESPIRATOR APPARATUS

TECHNICAL FIELD

This invention relates to a respirator apparatus in which breathing gas is supplied periodically to a patient through a supply line. A breathing frequency valve, appropriately controlled by an electromagnet, is installed in the supply line to periodically supply gas to the patient during certain intervals of time when the patient breathes in, separated by interlying intervals of time when the gas supply is interrupted and the patient breathes out.

BACKGROUND ART

Breathing frequency valves incorporated in the patient supply line typically have been controlled by signals emitted from a programmer to the valve so that the valve is open during only a certain portion, appropriately 22%, of a breathing cycle. During the remaining part of the breathing cycle, the valve must be closed. In some commonly employed respirators, the pressure in the gas line to the catheter which is introduced into the lungs is in the range of about $10.10^3$–$150.10^3$ Pa during the inspiration phase, that is, the phase during a respiration cycle when breathing gas is supplied to the patient. During the following expiration phase, the pressure in the gas line falls appreciably, so that when the expiration passages are completely free, it should have dropped to below about $2.10^3$ Pa after only half the respiration cycle. Occasionally, however, the expiratory passages can be blocked by a clot of phlegm or the like. In such circumstances, it is absolutely essential to switch off the respirator immediately, since otherwise the lungs would be over expanded by the frequent inspirations, possibly leading to a fatal condition.

DISCLOSURE OF THE INVENTION

A principle object of the present invention is to provide a respirator apparatus in which the supply of breathing gas to the patient is terminated and an alarm is sounded when the patient is unable to expire properly.

A good and dependable arrangement to prevent the disadvantages of prior art apparatuses is obtained in the apparatus according to the invention as specified in the appended claims. A particular advantage of the present invention is that it does not require the introduction of an extra air line into the lungs of the patient in addition to the supply line. Thus, the catheter introduced in the patient's lungs can have very small dimensions, for example, an inside diameter of 1.7–3.5 mm, which ensures greatly reduced discomfort for the patient.

BRIEF DESCRIPTION OF THE DRAWINGS

The invention will be described in greater detail with reference to the accompanying drawings, wherein.

BEST MODE FOR CARRYING OUT THE INVENTION

Figure 1:
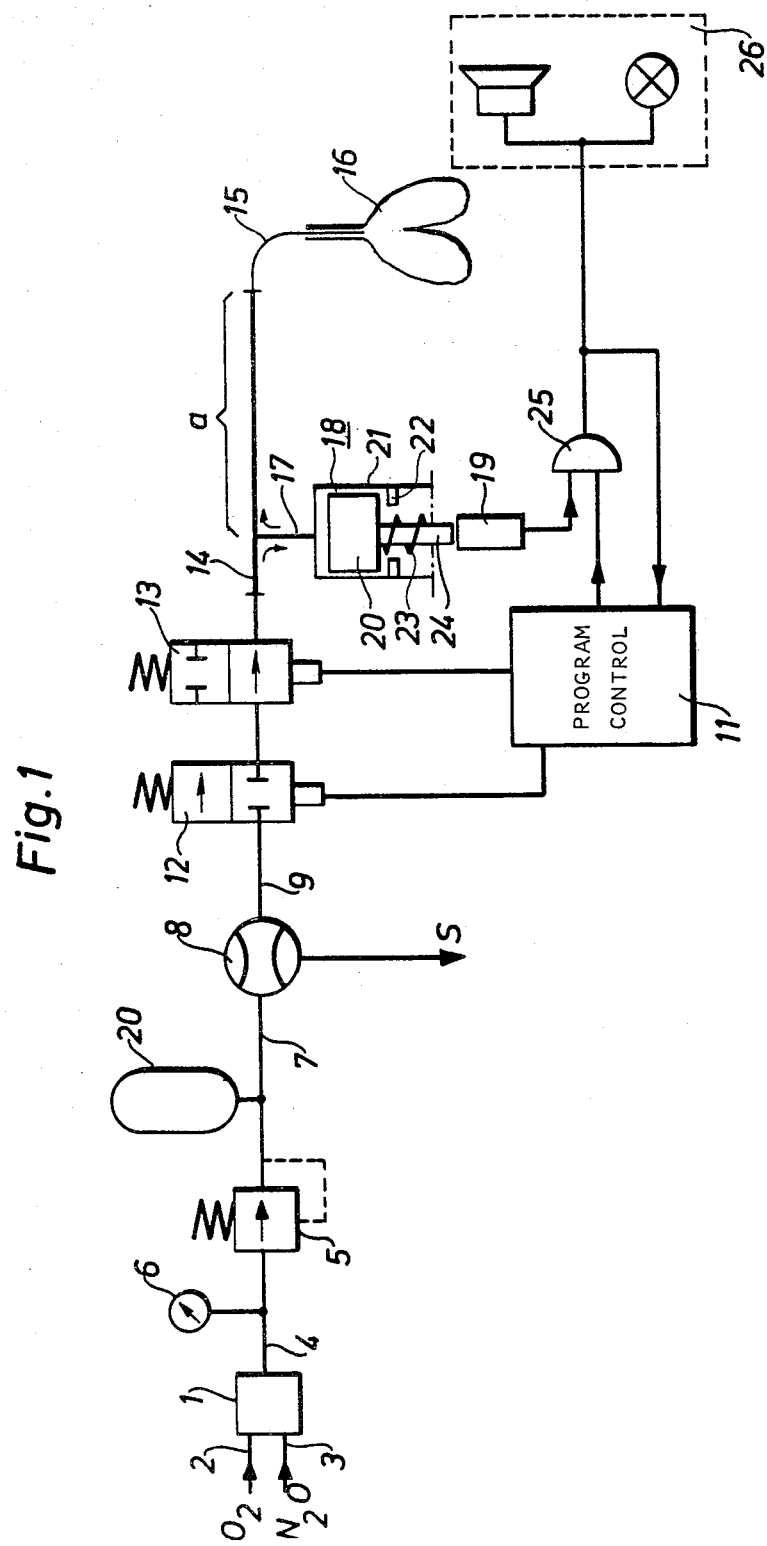
FIG. 1 shows a schematic diagram of the gas supply line in a respirator apparatus according to the invention.

The respirator apparatus shown in FIG. 1 comprises a gas mixer 1, to which gases can be supplied via lines 2 and 3. If the respirator is to be used as a breathing aid when performing an operation on a patient, these gases are often oxygen and an anesthetic gas such as laughing gas, respectively. The gas mixer 1 is connected to a pressure regulator 5 via a line 4. A pressure gauge 6 is also connected to the line 4. From the pressure regulator 5, the gas is conducted through a line 7 to a flow meter 8 which measures the total amount of breathing gas which flows through the line during a respiration cycle and also via line S to a unit (not shown) which emits an alarm if this amount should exceed a predetermined value. A flow meter of this kind is described in Swedish Pat. application No. 77 13463-3. Also installed in the line is an accumulator in the form of a container 20, which is continuously charged with breathing gas through the pressure regulator 5 during the expiration intervals and supplies gas to the patient through lines 7 and 9 during the inspiration intervals.

The gas leaving the flow meter 8 via the line 9 passes through two valves 12 and 13 which are connected in series. The valves 12 and 13 are biased by pressure springs shown on the drawing to their respective normally open and normally closed positions, and are moved against the action of the pressure springs, appropriately by electromagnets. The valve 12 is normally kept open during inspiration intervals of the patient and its electromagnet is activated to close the valve during the expiration phases, thereby facilitating expiration by the patient. The valve 12 is controlled by programmer 11. The components mentioned above are mentioned merely in order to describe the general function of a respirator and thus do not comprise an integral part of the present invention.

A valve 13 is connected in series with the valve 12 and serves as a warning and safety valve open only when its electromagnet is activated. Power to its electromagnet is interrupted by the programmer upon indication of too high pressure in the patient's lungs. The sequence of valves 12 and 13 in the line 9 has no significance. The gas leaving the valve 13 flows in one direction via a gas line 14 to a thin catheter 15 which is introduced into the lungs 16 of a patient. Connected to the line 14 at a distance a from the catheter is a branch line 17, the other end of which terminates in a pressure sensor 18, preferably of the kind which actuates a position transducer 19 in response to a sensed pressure within a relatively large pressure range, for example between 1 and $200.10^3$ Pa and inactivates the transducer in response to a drop in pressure below a preselected low limit for pressure. The low limit should moreover be easily adjustable.

One embodiment of a pressure transducer of this kind is shown in FIG. 1 and comprises a piston 20 which slides in a cylinder 21 against the action of an adjustable spring 23 towards a stop 22, in response to gas pressure in the line 14. The piston 20 is provided at the bottom with an operating rod 24 which actuates the position transducer 19 when the piston rests against the stop 22. The position transducer 19 may be of any kind whatsoever which is sensitive to changes in the position of an element. For example, it may be an inductive position sensor, comprising a reed switch which can be closed or opened by a magnet attached to the rod 24; it may comprise a light source and a light indicator in which the beam of light rays between these elements is interrupted by the rod 24 when the piston rests against its stop; it may comprise a switch actuated by the rod, and so forth as will be understood by those skilled in the art.

The signal produced by the position transducer 19 is a digital "1" when the transducer is actuated and a digital "0" signal otherwise. This signal is fed to one of the inputs of an AND gate 25, the other input of which is connected to an output on the programmer 11. This programmer output gives a "1" signal only after the inspiration phase of a respiration cycle and only after a delay until a point of time during the expiration phase occurring after that at which the pressure in the gas line 14 normally would have fallen to the pressure prevailing in the lungs. The point of time at which this occurs is dependent upon the length of the line 14 and of the size of the catheter 15. A practicable value of the length a of the line 14 between branch line 17 and the catheter 15 is 1 m, but it is also possible to use a line which is approximately 2 m long. It is appropriate if the "1" signal from the programmer 11 occurs during the latter portion, such as the last third of the expiration phase but it may also occur even earlier, for example after half the respiration cycle. If the position transducer 19 is still actuated due to high gas pressure acting on the pressure sensor 18 when the "1" signal issues from the programmer, a "1" signal will be fed from the AND gate 25 back to an input in the programmer 11. In response to this signal, programmer 11 will switch off the operating current to the electromagnet of the valve 13 causing the valve to close and activating an alarm unit 26 such as an acoustic alarm and/or an optical alarm.

Figure 2:
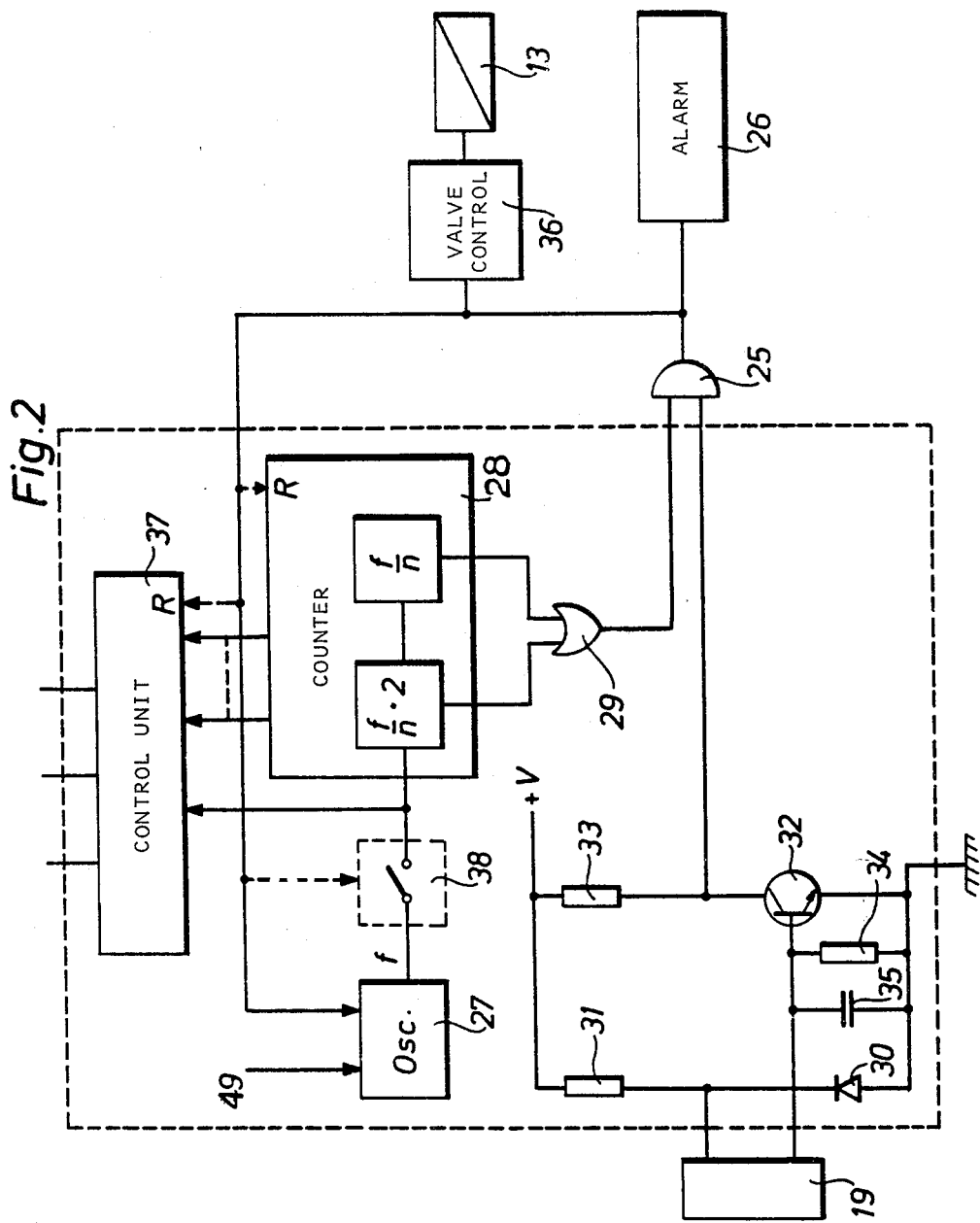
FIG. 2 shows a schematic diagram of a portion of the programmer used in the invention and also an embodiment of a position transducer used for valve control.

FIG. 2 shows one embodiment of that part of the programmer 11 which relates to the invention. An oscillator 27 feeds a square wave signal with a frequency of f to a counter 28. The frequency f may in certain cases be made variable through control by an input 49 on the oscillator 27. The artificial breathing frequency for a respirator may be selected within fairly wide limits, for example between 8 and 80 respirations per minute. In an exemplary case with 60 respirations per minute, a suitable frequency of the oscillator is 128 Hz. The counter 28, on one of its outputs, issues a square wave signal with a frequency of f/n, where n is an appropriate integer selected so that the frequency f/n will be established at the desired breathing frequency. In the example mentioned above, n is then chosen as 128. On the second output, the counter 28 emits a signal with a frequency of 2 f/n. Each of these outputs from the counter 28 is fed to its own input on a NOR gate 29, which then on its output gives a "1" signal during the last quarter of a respiration cycle. The output from the counter 29 is also fed to a unit 37 for control of the other functions of the respirator, and the phase positions for the various control signals are selected so that a "0" signal on the outputs connected to the NOR gate appears only during the end of the expiration phase of the respiration cycle. The output signal from the NOR gate 29 is fed to one of the inputs of the AND gate 25.

The position transducer of the embodiment shown in FIG. 2 comprises an inductive transducer of a kind commonly available on the market. It comprises an oscillation circuit which normally oscillates but which ceases to oscillate when an iron object comes into its immediate vicinity. Rod 24 may be made from carbon and provided with an end portion of iron. Transducer 19 and the pressure sensor 18 are so mounted in relation to each other that the oscillation circuit of the transducer does not oscillate when the piston 20 rests against the stop 22. One of the terminals of the transducer 19 is connected to a point on a conductor between a zener diode 30 and a resistor 31 which, in turn, are connected in a series between ground potential and the drive voltage V. The other terminal of transducer 19 is connected to the base of an NPN transistor 32, the emitter of which is connected to ground and the collector of which is connected via a collector resistor 33 to the drive voltage V. A resistor 34 is connected between the base of the transistor and ground. A relatively large capacitor 35 is connected in parallel with the resistor 34 to prevent ripple from the transducer 19 from influencing the transistor 32.

As long as the output of the transducer oscillates, the resistance of the transducer is so low that the base of the transistor 32 experiences a voltage which is essentially equal to the zener voltage of the zener diode 30. This voltage is selected so that the transistor 32 then becomes saturated and a "0" signal is fed to the second input of the AND gate 25. However, as soon as the piston reaches its bottom position, the output of the transducer 19 ceases to oscillate and its resistance then increases so that the base of the transistor 32 experiences such a low potential that the transistor is cut off. The potential on the second input of the AND gate 25 is then applied on a high potential, which gives a "1" signal.

As evident from FIG. 1, the piston 20 is pressed to its bottom position by the high pressure in the line 14 during the inspiration phase. This pressure is different on different occasions partly in consequence of the fact that different catheter sizes can be chosen for different patients and partly because different patients require different amounts of breathing gas during the inspiration phase. It is evident that the arrangement according to the invention would work regardless of the pressure actually occurring in the gas line 14 during the inspiration phase. This condition is also satisfied by the arrangement according to the invention since the pressure in the lungs is always higher during the inspiration phase than during the expiration phase and the pressure in the gas line 14 would, in principle, during the later part of the expiration phase, have adopted the pressure prevailing in the lungs. The pressure spring 23 is adjusted so that it moves the piston 20 away from the stop 22 at the pressure level corresponding to the pressure in the lungs which, according to the doctor's instructions, may not be exceeded during the expiration phase of respiration.

In the circuit according to the embodiment shown in FIG. 2, a "1" signal will occur on the output of the AND gate 25 only if the transistor 32 is still cut off; that is, if the transducer 19 is actuated by the rod 24, during the last quarter of the respiration cycle, since a "1" signal is then obtained from the NOR gate 29. A "1" signal from the AND gate 25 can either be fed to an input on the oscillator 27 and lock this in the phase position which it then occupies or else be fed to open by regulation a controllable contact 38 in the output conductor from the oscillator. In addition, the output signal from the AND gate is fed to a control input on a valve control 36 which supplies current to the electromagnet of valve 13 in order to switch off the drive current to the electromagnet and to keep this closed for as long as a "1" signal remains on the output of the AND gate. The alarm unit 26 is also actuated by the "1" signal from the gate 25 as previously mentioned.

The supply of breathing gas to the patient is switched off and the entire function of the respirator is thus frozen until the pressure in the gas line 14 has fallen to below the set reaction value for the pressure sensor. From this point onward, the respirator continues to work from the working position at which it was stopped.

It is also possible to arrange for the counter 28 to be zeroed and to set the control 37 of the other functions of the respirator at a suitable control phase upon receipt of a "1" signal from the AND gate 25, which has been marked with broken dashed lines to resetting inputs R on blocks 28 and 37.

Several different modifications are possible within the scope of the inventive concept. In particular, the output signal from the AND gate 25 can be arranged to block the signals from the counter 28 and the control 37 of the other functions of the respirator, whereby the programmer 11 can be said to be constantly running and a "1" signal from the AND gate 25 blocks the operation of the respirator from a constantly running programmer.

Having described my invention in sufficient detail to enable those skilled in the art to make and use it,

I claim:

1. A respirator apparatus, comprising:
   a source of breathing gas;
   a breathing catheter having an open end for introducing breathing gas into the lungs of a patient and an opposite end;
   gas line means connected between said source and said opposite end of said breathing catheter for providing one way flow from said source to said breathing catheter;
   means for establishing timed respiration cycles, each cycle having an inspiration phase and an expiration phase, and for permitting flow of said breathing gas through said catheter, whereby a maximum lung pressure is produced during each inspiration phase;
   means connected to said gas line means for sensing the pressure of said breathing gas;
   means responsive to said means for establishing timed respiration cycles and to said means for sensing pressure, for producing a control signal when said pressure remains higher than a predetermined level below said maximum lung pressure during the latter portion of each said expiration phase; and means responsive to said control signal for preventing flow of said breathing gas through said gas line means and catheter during the subsequent inspiration phase.

2. Apparatus according to claim 1, wherein said pressure sensing means comprises a cylinder, a piston slidable within said cylinder, adjustable means for biasing said piston toward one end of said cylinder against the pressure in said catheter and stop means for limiting movement of said piston in response to said pressure, further comprising transducer means responsive to said sensing means when said piston rests against said stop means, said producing means being responsive to said transducer means.

3. Apparatus according to claim 2, further comprising means responsive to said control signal for locking said establishing means in its existing phase when pressure above said predetermined level is detected during said latter portion of said expiration phase, until said pressure drops below said predetermined level.

4. Apparatus according to claim 2, further comprising means responsive to said control signal for resetting said establishing means when pressure above said predetermined level is detected during said latter portion of said expiration phase.

5. Apparatus according to claim 2, further comprising means responsive to said control signal for blocking the output of said establishing means when pressure above said predetermined level is detected during said latter portion of said expiration phase.

6. Apparatus according to claim 1, further comprising means responsive to said control signal for locking said establishing means in its existing phase when pressure above said predetermined level is detected during said latter portion of said expiration phase.

7. Apparatus according to claim 6, further comprising means responsive to said control signal for resetting said establishing means when pressure above said predetermined level is detected during said latter portion of said expiration phase.

8. Apparatus according to claim 7, further comprising means responsive to said control signal for blocking the output of said establishing means when pressure above said predetermined level is detected during said latter portion of said expiration phase.

9. Apparatus according to claim 1, further comprising means responsive to said control signal for resetting said establishing means when pressure above said predetermined level is detected during said latter portion of said expiration phase.

10. Apparatus according to claim 9, further comprising means responsive to said control signal for blocking the output of said establishing means when pressure above said predetermined level is detected during said latter portion of said expiration phase.

11. Apparatus according to claim 1, further comprising means responsive to said control signal for blocking the output of said establishing means when pressure above said predetermined level is detected during said latter portion of said expiration phase.

12. Apparatus according to claim 11, further comprising means responsive to said control signal for locking said establishing means in its existing phase when pressure above said predetermined level is detected during said latter portion of said expiration phase, until said pressure drops below said predetermined level.

* * * * *